(12) United States Patent
Webler

(10) Patent No.: US 6,955,657 B1
(45) Date of Patent: Oct. 18, 2005

(54) INTRA-VENTRICULAR SUBSTANCE DELIVERY CATHETER SYSTEM

(75) Inventor: William Earl Webler, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 422 days.

(21) Appl. No.: 10/038,788

(22) Filed: Dec. 31, 2001

(51) Int. Cl.⁷ .................. A61M 31/00; A61M 37/00; A61M 25/00; A61N 1/00; A61N 1/04
(52) U.S. Cl. .................. 604/95.04; 604/527; 607/122
(58) Field of Search .................. 604/93.01, 95.01, 604/95.04, 164.01, 164.12, 523, 524, 525, 604/526, 527, 528; 600/433, 434, 435, 585; 607/115, 116, 119, 122, 126

(56) References Cited

U.S. PATENT DOCUMENTS

| | | | |
|---|---|---|---|
| 4,723,936 A | 2/1988 | Buchbinder et al. | |
| 4,757,827 A | 7/1988 | Buchbinder et al. | |
| 4,813,434 A | 3/1989 | Buchbinder et al. | |
| 4,815,478 A | 3/1989 | Buchbinder et al. | |
| 5,114,414 A | 5/1992 | Buchbinder et al. | |
| 5,125,895 A | 6/1992 | Buchbinder et al. | |
| 5,230,348 A | 7/1993 | Ishibe et al. | |
| 5,415,633 A | 5/1995 | Lazarus et al. | |
| 5,441,483 A | 8/1995 | Avitall | |
| 5,662,621 A | 9/1997 | Lafontaine | |
| 5,730,741 A * | 3/1998 | Horzewski et al. | 606/1 |
| 5,755,704 A | 5/1998 | Lunn | |
| 5,797,870 A | 8/1998 | March et al. | |
| 5,820,592 A | 10/1998 | Hammerslag | |
| 5,873,842 A | 2/1999 | Brennen et al. | |
| 5,876,373 A | 3/1999 | Giba et al. | |
| 5,964,971 A | 10/1999 | Lunn | |
| 5,997,525 A | 12/1999 | March et al. | |
| 6,009,349 A * | 12/1999 | Mouchawar et al. | 607/6 |
| 6,045,565 A | 4/2000 | Ellis et al. | |
| 6,102,887 A | 8/2000 | Altman | |
| 6,120,520 A | 9/2000 | Saadat et al. | |
| 6,126,654 A | 10/2000 | Giba et al. | |
| 6,129,649 A | 10/2000 | VanTassel et al. | |
| 6,179,809 B1 | 1/2001 | Khairkhahan et al. | |
| 6,224,584 B1 | 5/2001 | March et al. | |
| 6,238,406 B1 | 5/2001 | Ellis et al. | |
| 6,267,746 B1 | 7/2001 | Bumbalough | |
| 6,327,492 B1 * | 12/2001 | Lemelson | 600/434 |

* cited by examiner

Primary Examiner—Nicholas D. Lucchesi
Assistant Examiner—Mark K. Han
(74) Attorney, Agent, or Firm—Blakely, Sokoloff, Taylor & Zafman LLP

(57) ABSTRACT

A guide catheter and a needle catheter are disclosed. The guide catheter construction provides for maximum articulation of the deflectable tip and maximum torque response during rotation. The needle catheter may include a release mechanism that imparts a sudden force to the needle in order to facilitate tissue penetration.

26 Claims, 7 Drawing Sheets

US 6,955,657 B1

INTRA-VENTRICULAR SUBSTANCE DELIVERY CATHETER SYSTEM

FIELD OF THE INVENTION

This invention relates generally to catheters, and more particularly to catheters used to navigate a vascular system in order to access a desired location within a body.

BACKGROUND

It is increasingly important that a physician or surgeon delivering substances, such as drugs, is able to efficiently and accurately locate the desired target tissue for effective delivery of the substance. This is particularly true when the concentration of the substance required at the target site cannot be safely or effectively achieved by introduction of the substance to a location remote from the target site. Moreover, the physician may only want to treat the diseased portion of an organ or tissue and avoid treating the healthy portions.

Such localized treatment is necessary not only for substance delivery but also for other treatments, including myocardial revascularization. Myocardial revascularization is a procedure in which "holes" are formed in ischemic ventricular tissue in order to increase blood flow to the treated area. It is thought that the tissue damage (e.g., holes) encourages growth of blood vessels in the treated area. Similar to substance delivery, myocardial revascularization is a procedure that is preferably performed only on specific areas that require treatment.

One common target site is the left ventricle of the human heart. The left ventricle is particularly important since the left ventricle supplies blood to the entire body with the exception of the lungs. Thus, if the left ventricle is compromised, a patient will become very ill and may possibly die. The severity of the diseases of the left ventricle coupled with the importance of localized diagnosis and treatment within the left ventricle render the ability to effectively and accurately access specific portions of the left ventricle extremely important.

SUMMARY

The various embodiments described herein use a deflectable guide catheter in conjunction with a needle catheter to access the vascular system, including the heart, of a patient. The guide catheter has a deflecting tip section with a minimized radius of curvature to maximize the area that can be accessed by the device. In addition, the construction of the guide catheter provides for maximum torque response when rotating the guide catheter. In some embodiments, the needle catheter includes a mechanism to impart a sudden force on the needle to improve tissue penetration.

DESCRIPTION OF THE DRAWINGS

Various embodiments are illustrated by way of example and not by way of limitation in the figures of the accompanying drawings in which like references indicate similar elements. It should be noted that references to "an", "one", or "various" embodiments in this disclosure are not necessarily to the same embodiment, and such references mean at least one.

DETAILED DESCRIPTION

In the following description, for purposes of explanation, numerous specific details are set forth in order to provide a thorough understanding of the various embodiments. It will be apparent, however, to one skilled in the art that the various embodiments may be practiced without some of these specific details. The following description and the accompanying drawings provide examples for the purposes of illustration only. However, these examples should not be construed in a limiting sense as they are merely intended to provide exemplary embodiments, rather than to provide an exhaustive list of all possible implementations.

Figure 1:
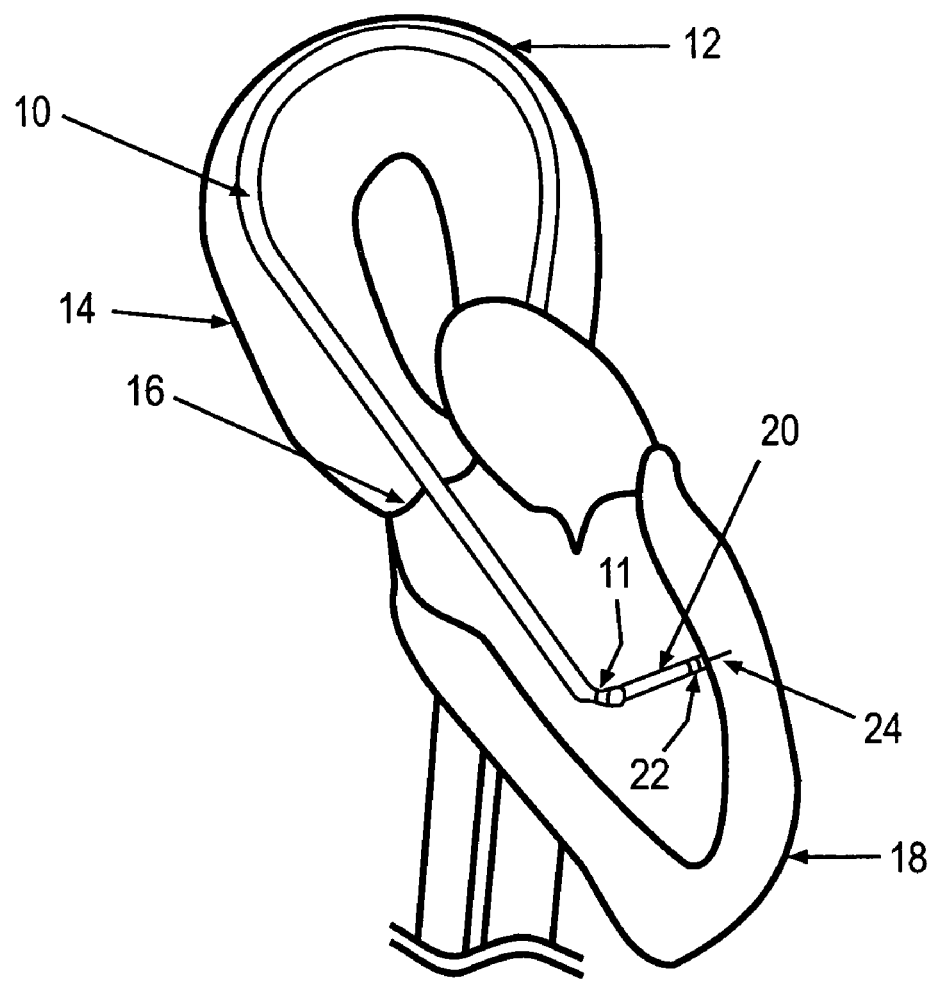
FIG. 1 shows an embodiment with the guide catheter in a deflected position and the needle catheter protruding from the guide catheter.

Referring now to FIG. 1, the distal end of an embodiment is shown, which includes guide catheter 10 and needle catheter 20. Although guide catheter 10 may be used throughout the body of a patient, guide catheter 10 is shown in use within the left ventricle of a human heart. For example, guide catheter 10 may be introduced into the body of a patient through the femoral artery and directed over aortic arch 12, through aorta 14 and aortic valve 16, and into left ventricle 18.

Once inside left ventricle 18, the distal portion of guide catheter 10 may be advanced, retracted, deflected, and/or rotated in order to position needle catheter 20 in a desired location in order to deliver a substance (e.g., injection) or conduct a procedure. If tissue penetration is desired, needle 24 disposed in the distal end of needle catheter 20 is moved to a deployed position as shown in FIG. 1.

Tip electrode 22 disposed on the distal end of needle catheter 20 is used to determine whether contact with the wall of left ventricle 18 has been made, and if so, whether full needle penetration has been made. One way this is accomplished is that when tip electrode 22 contacts live ventricular tissue, there is an amplitude increase in an electrocardiogram ("ECG") produced by an electrocardiograph or monitor (not shown) electrically coupled to tip electrode 22 and to reference electrode 11.

Thus, if there is an initial ECG amplitude increase that indicates contact and a subsequent decrease in ECG amplitude upon the extension of needle 24, then contact between tip electrode 22 and the ventricular wall has been lost. Such a loss of contact can mean that needle 24, upon deployment, did not penetrate the ventricular wall and that needle catheter 20 was pushed away from the ventricular wall. Alternatively, a loss of contact can mean that only partial needle penetration was achieved.

Tip electrode 22 can also be used to diagnose the ventricular tissue. For example, in one embodiment, healthy ventricular tissue typically results in a high amplitude ECG when contacted by tip electrode 22. Stunned (e.g., ischemic)

ventricular tissue and ventricular wall tissue with a reduced thickness are considered to be alive but not functioning properly. When either of these types of ventricular tissue is contacted by tip electrode 22, a high amplitude ECG is typically seen. Dead ventricular tissue and scar tissue, on the other hand, typically each yield an unchanged or low amplitude ECG when contacted by tip electrode 22.

When ECG amplitude information is combined with ventricular wall motion information, the stunned ventricular tissue may be differentiated from healthy tissue. Specifically, healthy tissue will typically exhibit greater and more rapid wall motion than stunned tissue. Wall motion information may be collected prior to the procedure using ultrasonic, magnetic resonance imaging, and/or various X-ray techniques. Wall motion information may also be collected during the procedure by fluoroscopic observation of tip electrode 22 while in contact with the ventricular wall or by incorporation of a location sensor or an accelerometer (not shown).

In various embodiments, a reference electrode could be coupled to the distal portion of guide catheter 10, a distal portion of needle catheter 20, or an outer surface of the body of the patient. However, the embodiment shown in FIG. 1 has reference electrode 11 (also referred to in some embodiments as an anchor element) disposed on a distal portion of guide catheter 10.

Figure 2:
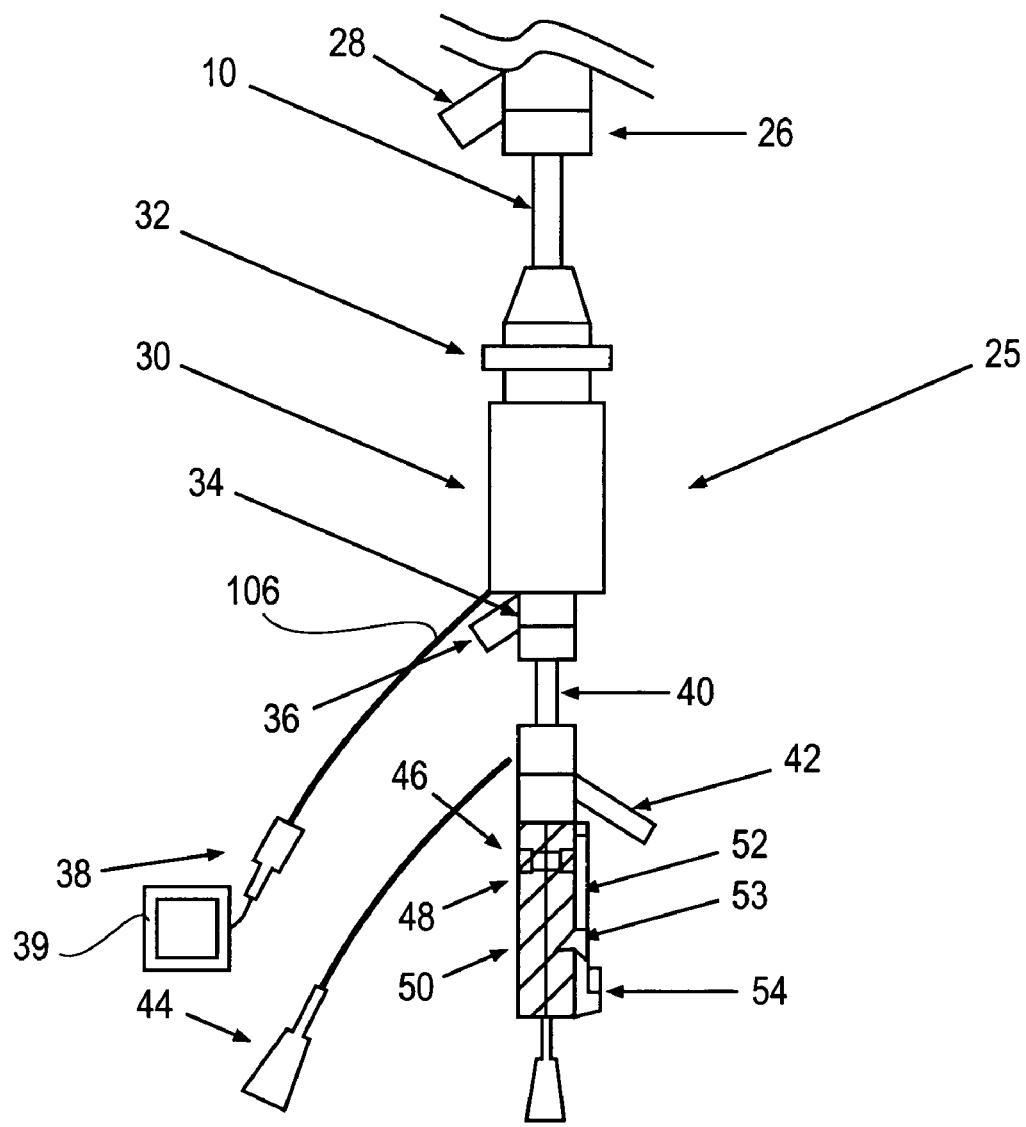
FIG. 2 shows a side view of the handle portion of the embodiment shown in FIG. 1.

Among other items, FIG. 2 shows handle 25, which is used to control guide catheter 10. Handle 25 includes grip 30, which is used to control the rotational and longitudinal position of guide catheter 10. Handle 25 also includes deflection control 32, which is used to control the deflection of the distal portion of guide catheter 10. The rotational movement of guide catheter 10 and the deflection mechanism will be described more fully below.

The embodiment shown in FIG. 2 also includes the proximal portion of an introducer sheath (used to introduce a catheter into the body of a patient) that has adjustable friction valve 26 and flush port 28. Flush port 28 provides a means for flushing the introducer sheath.

Adjustable friction valve 26 advantageously allows the operator to set the friction level exerted on guide catheter 10 at a level appropriate for the circumstances. For instance, if the catheter is in a position that requires no movement, the operator can essentially lock adjustable friction valve 26 to prevent any rotational or longitudinal movement without affecting the ability of the operator to deflect the distal portion of guide catheter 10 or to longitudinally move needle catheter 20. However, the operator can also set adjustable friction valve 26 to a friction point where guide catheter 10 is movable only by a sufficient amount of force applied to guide catheter 10 by the operator. One example of an adjustable friction valve is a hemostasis valve commercially available from Advanced Cardiovascular Systems, Inc. under the name COPILOT.

The construction of guide catheter 10 provides for accurate positioning of guide catheter 10. For instance, guide catheter 10 comprises handle 25, described above, and a flexible body portion coupled to handle 25. The flexible body portion has dimensions suitable for insertion into and navigation through the body of a patient.

The flexible body portion defines lumen 98 therethrough. In various embodiments, Teflon liner 99 defines lumen 98 (see FIGS. 6 and 7). In use, needle catheter 20 (see FIG. 1) is disposed within guide catheter lumen 98. It is worth noting here that although the embodiments disclosed herein focus mainly on guide catheter 10 as a separate entity from needle catheter 20, it is contemplated that the two catheters could be designed and constructed as a single catheter.

The flexible body portion of guide catheter 10 includes a distal portion and a proximal portion. The proximal portion, shown in FIG. 6, comprises flexible element 100 around lumen 98 and outer (e.g., first) braid 102 disposed over flexible element 100. Flexible element 100 is at least one of a coil and a second braid.

If a coil, flexible element 100 is at least one of a single coil and a multi-filar coil (e.g., having multiple coil elements wound together to form a coil). In another embodiment, flexible element 100 is an eight wire braid having 140 picks/inch (a pick is a point where the wires cross when observed along the longitudinal axis of the braid) constructed with flatwire that has a thickness of 0.001 inches and a width of 0.005 inches.

Regardless of whether flexible element 100 is a coil or a braid, flexible element 100 prevents compression of the flexible body portion and prevents the collapse of outer braid 102. It is important to reduce the amount of compression experienced by the flexible body portion since lower compression results in more accurate navigation and placement of guide catheter 10 and improved deflection response.

Outer braid 102 disposed over the flexible element 100 is designed to have a maximum torque response, which means that torsional force applied at one end of the flexible body portion will result in an equal rotational movement along the length of the flexible body portion. A maximized torque response is desirable in various embodiments since a low torque response could result in the flexible body portion acting as a torsional spring, storing rotational force that will eventually be released and cause a "whipping" motion. Such a loss of control is obviously undesirable when attempting to navigate a vascular system and position a guide catheter within the body of a patient.

In one embodiment, outer braid 102 is a sixteen wire braid having 40 picks/inch and is wound at an angle of approximately 55 degrees relative to the longitudinal axis of the flexible body portion. This "lay angle" of approximately 55 degrees has been experimentally determined to yield the maximum torque response for any given wire. During the experimentation, the total torque for a given guide catheter was determined by adding the torques produced by the braid (including torque produced by wires that lay to the right and the left), the liner (e.g., Teflon) beneath the braid, and the plastic coating disposed on the braid (discussed in more detail below).

Figure 6:
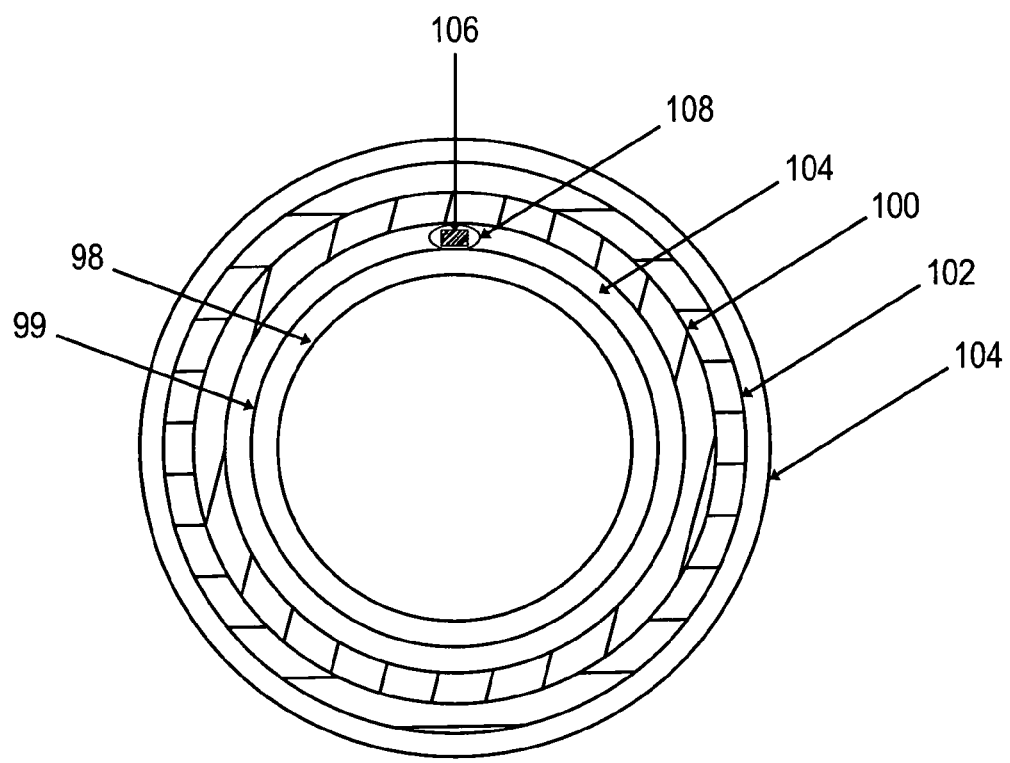
FIG. 6 shows a cross-sectional view of an embodiment of the proximal portion of a guide catheter.

The proximal portion of the flexible body portion is impregnated with first plastic coating 104 (shown in FIG. 6). The distal portion of the flexible body portion (having no flexible element or braid) is coated with second plastic coating 112 (see FIG. 7). In various embodiments, second plastic coating 112 is more flexible than first plastic coating 104 on the proximal portion. The flexibility of both the proximal and distal portions can be varied based on the type and thickness of plastic coating used.

The difference in flexibility between the proximal portion and the distal portion of the flexible body portion advantageously allows for deflection of the distal portion for navigation and positioning of the guide catheter. The distal portion is deflected by tendon wire 106 having a distal end attached to anchor element 11 (FIG. 7) and a proximal end attached to handle 25 such that manipulation of deflection control 32 results in deflection of the distal portion of the flexible body portion. Tendon wire 106 can be attached to either the inner diameter or the outer diameter of anchor element 11 in order to impart a deflecting force on anchor element 11.

Tendon wire 106 can be disposed within Teflon sheath 108 located outside of guide catheter lumen 98 but within flexible element 100 and outer braid 102. In one embodiment, tendon wire 106 is a stainless steel wire having a diameter of 0.008 inches.

In various embodiments, tendon wire 106 is coupled to deflection control 32 by a pulley, which gives a mechanical advantage when manipulating deflection control 32 in order to deflect the distal portion of the flexible body portion. Furthermore, tendon wire 106 can be disposed in a straight line along the length of guide catheter 10 or can be spiraled along the length of guide catheter 10.

For instance, the proximal portion may have tendon wire 106 straight or loosely spiraled while the more distal portions of the proximal portion may have a tighter spiral in order to avoid bias towards any one direction. Such a bias can occur around a curve such as the aortic arch. However, a tight spiral can prevent bias and the "whipping" associated with such bias. In addition, spiraling allows certain rotational orientations that would otherwise be difficult or impossible to attain and maintain around a curve.

Figure 7:
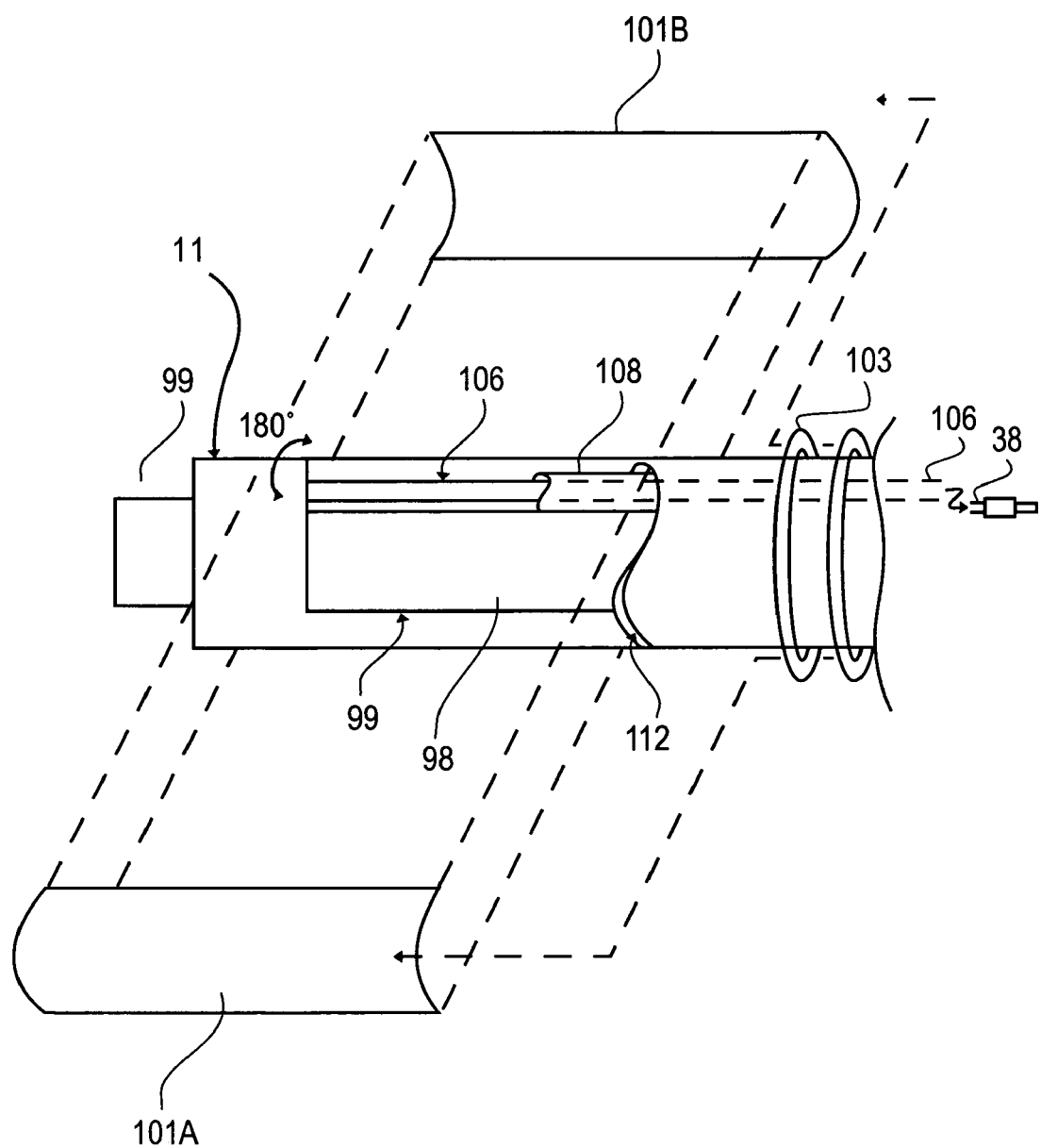
FIG. 7 shows the distal portion of one embodiment of a guide catheter.

Anchor element 11 (see FIGS. 1 and 7) is disposed in the distal portion of the flexible body portion and can be at least one of a ring (as shown in FIG. 7) and an electrode. In various embodiments, anchor element 11 and tendon wire 106 are constructed from electrically conductive material so that the tendon wire/anchor element assembly serves as part of the deflection mechanism and as a reference electrode, as discussed above. For example, FIG. 2 shows electrical interface 38 coupled to the tendon wire so that 39 can receive an electrical signal from tendon wire 106 to be used as a reference signal to be compared with the electrical signal obtained from tip electrode 22.

In various embodiments, a third plastic coating is disposed on an area just proximal to anchor element 11. The third plastic coating is stiffer than second plastic coating 112 and prevents anchor element 11 from moving proximally due to stresses experienced during deflection. Furthermore, if tendon wire 106 is attached to the outer diameter of anchor element 11, the third plastic coating reduces the peel forces on the bond between tendon wire 106 and anchor element 11 by increasing the radius of curvature (e.g., decreasing the deflection) in the area of the tendon wire/anchor element bond.

In various embodiments, the distal portion of guide catheter 10 has a first piece of elastically deformable material disposed on a first area. In addition, a second piece of elastically deformable material is disposed on a second area of the distal portion of guide catheter 10. The second area being approximately 180 degrees from the first area. Thus, the two pieces of elastically deformable material lay on opposite "sides" of the distal portion of guide catheter 10. The two pieces of elastically deformable material are formed from material having a higher modulus than the plastic coating (e.g., jacket material) that the elastically deformable material displaces. FIG. 7 shows first piece 101A of elastically deformable material and second piece 101B of elastically deformable material connected to the distal portion of guide catheter 10.

With the two pieces of elastically deformable material disposed 180 degrees from each other, the tendon wire can be attached at a point 90 degrees from either of the pieces of elastically deformable material. This configuration and the higher modulus of the elastically deformable material create a deflection bias in the areas of the distal portion of guide catheter 10 that do not have the pieces of elastically deformable material. Thus, the deflection characteristics of the distal portion of guide catheter 10 can be modified based on the elastically deformable material used and the placement of the tendon wire relative to the elastically deformable material.

In other embodiments, a coil of elastically deformable material can be used either in place of or in conjunction with the two pieces of elastically deformable material described above. If used in conjunction with the two pieces of elastically deformable material, the coil can be coupled either to the interior or exterior portions of each of the two pieces of elastically deformable material. FIG. 7 shows coil 103 that is connected to exterior portions of each of first piece 101A of elastically deformable material and second piece 101B of elastically deformable material.

It is worth noting that the elastically deformable material may be attached to the outer portions of guide catheter 10, imbedded or melted into the second plastic coating, attached to a coil or braid structure, and/or contain multiple mounting structures. In general, these "splint" configurations can be used to create a restoring force that generates more stable elastic deformation of the distal portion of guide catheter 10 in a desired direction. The restoring force also facilitates the return of the distal portion of guide catheter 10 to an undeflected state upon release of the tendon wire force. Such a restoring force additionally prevents permanent deformation of the distal portion of guide catheter 10.

Figure 4:
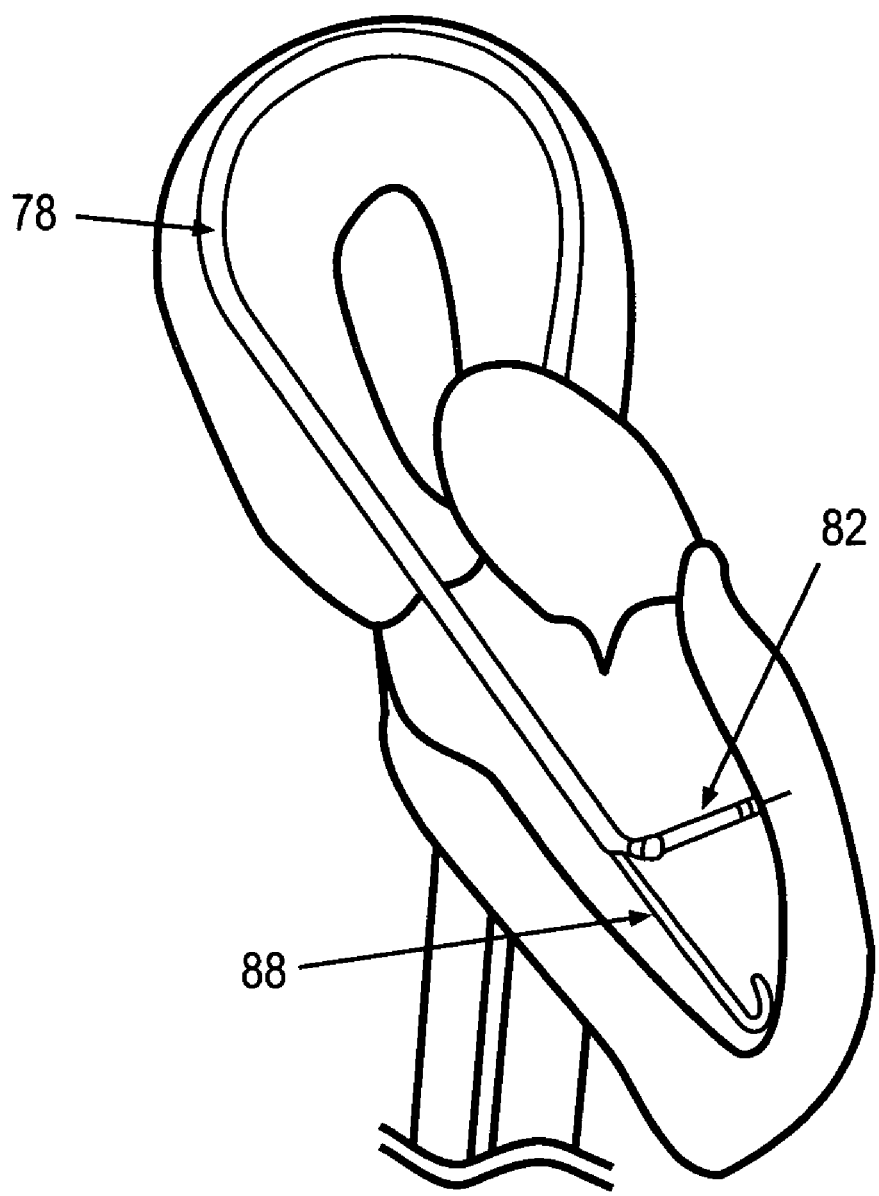
FIG. 4 shows an embodiment of the guide catheter that has a second lumen to accommodate a stabilizing member that protrudes from the guide catheter and rests in the apex of the ventricle.

FIG. 4 shows an example of an embodiment with stabilizing member 88, which is used as a reference point for the flexible body portion when moving guide catheter 78 and needle catheter 82. In embodiments with such a stabilizing member, the flexible body portion of guide catheter 78 further includes a second lumen and elongate stabilizing member 88 disposed within the second lumen such that the distal end of the stabilizing member protrudes from the distal end of the second lumen. The distal end of stabilizing member 88 can be curved as shown in FIG. 4 or can be curled in the shape of a pig tail in order to prevent injuring tissue.

In use, the distal end of stabilizing member 88 is placed and retained in a location within the body of a patient for reference while needle catheter 82 is used to diagnose and treat surrounding tissue. In FIG. 4, the apex of the left ventricle serves as the reference point for movement of guide catheter 78 and needle catheter 82. As mentioned above, although the left ventricle is used for illustration, embodiments with stabilizing member 88 could be used in other portions of the body.

Besides use of a stabilizing member, there are other ways to assist an operator in assessing the position of the guide catheter within the body of a patient. For example, a location sensor can be disposed in the distal end of the flexible body portion of the guide catheter. The location sensor could indicate the position of the distal end of the guide catheter by at least one of an electromagnetic mapping system, a radio frequency system, and an ultrasonic mapping system.

Similarly, such a location sensor could be disposed in the distal end of the needle catheter. Moreover, portions of the guide catheter and/or needle catheter can be made of radiopaque material so that the radiopaque portions are detectable with the use of a fluoroscope.

Focusing now on the needle catheter, FIG. 1 shows needle catheter 20 protruding from an opening in guide catheter 10 with needle 24 in a deployed position into a wall of left ventricle 18. Needle catheter 20 is disposed within the lumen of guide catheter 10 and can be moved longitudinally relative to guide catheter 10 in the embodiment shown. Thus, in use, needle catheter 20 may be inserted along with guide catheter 10 into left ventricle 18 or may be inserted through guide catheter 10 once guide catheter 10 is positioned within left ventricle 18. Alternatively, guide catheter 10 and needle catheter 20 can be constructed as one catheter that is inserted and positioned as a single device.

The construction of needle catheter 20 allows for the transfer of substances through the body of needle catheter 20. Examples of substances that may be delivered include drugs, pharmaceutical agents, fluids, proteins, polypeptides, gene therapy material, cell therapy material, and deoxyribonucleic acid ("DNA").

Figure 3:
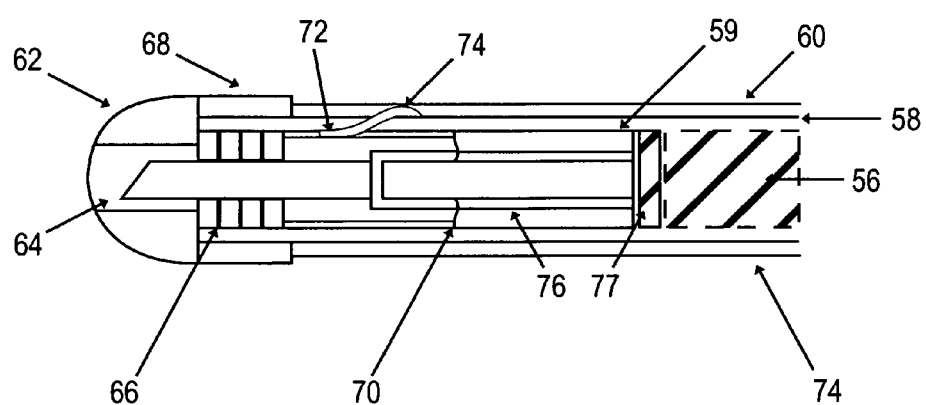
FIG. 3 shows a cross-sectional view of the distal end of an embodiment of the needle catheter.

An embodiment of the distal end of needle catheter 20 of FIG. 1 is shown in FIG. 3. Specifically, needle catheter 20 includes duplex spring 56 (e.g., two springs wound together, sometimes in opposite directions) impregnated with a polyethylene/ethylene acrylic acid blend. Duplex spring 56 defines a lumen through which substances can be delivered.

In order to give structural support to duplex spring 56, braided shaft 58 is disposed over duplex spring 56. Braided shaft 58 may be double braided and may also have Teflon sheath 59 disposed on the inner diameter of braided shaft 58. Finally, plastic coating 60 is disposed over braided shaft 58. Such a coating advantageously provides a smooth, flexible outer surface for the needle catheter.

Needle 64 is coupled to the inner diameter of duplex spring 56. In various embodiments, needle 64 is coupled to duplex spring 56 by welding or soldering. An electrical insulator is disposed between needle 64 and electrode 62, discussed below. In the embodiment shown, the electrical insulator is Teflon sheath 76 disposed over at least a portion of needle 64. Similarly, duplex spring 56 has Teflon sheath 77 to electrically insulate duplex spring 56 from electrode 62.

It is worth noting that although Teflon sheath 76 and Teflon sheath 77 are shown as distinct components, sheath 76 and sheath 77 may be constructed as a single sheath, layer, or component. Although Teflon is used herein as an insulator, other suitable insulators could be used. Alternatively, electrically insulative sheath 76 could be omitted so long as needle 64 was constructed out of a non-conductive material such as ceramic.

Electrode 62 (same as tip electrode 22 of FIG. 1) is disposed on the distal end of the needle catheter. Electrode 62 has an opening through which needle 64 is movable between a retracted position (seen in FIG. 3) and a deployed position. In the embodiment shown in FIG. 3, proximal end 70 of electrode 62 functions as a stop to prevent distal movement of needle 64 beyond the deployed position. For instance, once the distal end of duplex spring 56 contacts proximal end 70, needle 64 is in the fully deployed position and cannot move beyond the deployed position.

In various embodiments, electrode 62 has barbs 66 that aid in attachment of electrode 62 to the distal end of the needle catheter. Specifically, electrode 62 is inserted into Teflon sheath 59 until barbs 66 lie within the inner diameter of Teflon sheath 59. Ring 68 is placed over Teflon sheath 59 to tightly mesh Teflon sheath 59 into barbs 66. In various embodiments, ring 68 is welded to electrode 62.

Lead attachment 72 is electrically coupled to electrode 62 in order to obtain an electrical signal from electrode 62. In various embodiments, lead attachment 72 is coupled to lead wire 74, which can be any suitable conductor. In the embodiment shown, lead wire 74 is an insulated molybdenum wire coupled to electrode 62 (e.g., by lead attachment 72), fed out through a hole in braided shaft 58, and wrapped around braided shaft 58 before plastic coating 60 is disposed on braided shaft 58. The insulation on lead wire 74 could be, for example, polyimide, polyester, and/or Teflon.

As shown in FIG. 2, at the proximal end of the device, lead wire 74 is electrically coupled to electrical interface 44 so that an instrument can receive an electrical signal from electrode 62 through lead wire 74. Adjustable friction valve 34 allows the operator to set the friction level exerted on needle catheter 40 at a desired level. Flush port 36 provides a means for flushing guide catheter 10. Similarly, flush port 42 provides a means for flushing needle catheter 40.

A needle control assembly is coupled to the proximal end of the needle catheter. FIG. 2 shows an embodiment of a needle control assembly. The needle control assembly includes an elastically deformable element coupled to at least one of the duplex spring and the braided shaft of the needle catheter and a release mechanism. The release mechanism releasably engages the elastically deformable element when the elastically deformable element is in a position that corresponds to the needle being in a retracted position.

In the embodiment shown in FIG. 2, the elastically deformable element is spring 50. The release mechanism includes housing 46 with spring 50 disposed within housing 46. Stop 48 of the release mechanism is disposed within housing 46 and is coupled to the distal end of spring 50 and to at least one of the duplex spring and the braided shaft of the needle catheter.

The release mechanism further includes first latch 52 and second latch 54. First latch 52 is pivotally coupled to housing 46 and has a movable portion that is biased towards housing 46 by a spring, or the like. First latch 52 also includes an angled portion and a flat portion that form wedge-shaped protrusion 53 that extends into housing 46 (see FIG. 2). In operation, when spring 50 is compressed (e.g., moving the needle to the retracted position), stop 48 can move proximally past the angled portion of wedge-shaped protrusion 53.

Once past the angled portion, the distal end of stop 48 releasably engages the flat portion of wedge-shaped protrusion 53. Thus, first latch 52 holds spring 50 in a compressed state until released by the operator. In order to ensure that first latch 52 is not inadvertently released, second latch 54 is used to hold first latch 52 in place. Specifically, second latch 54 is pivotally coupled to housing 46 and has a movable portion biased towards housing 46. Second latch 54 releasably engages first latch 52 when the flat portion of first latch 52 is in contact with stop 48 in order to prevent first latch 52 from releasing stop 48.

Thus, an operator might retract needle 24 of FIG. 1 by compressing spring 50 of FIG. 2 and "locking" spring 50 in place with first latch 52 and securing first latch 52 with second latch 54. After the needle catheter is in a desired penetration location, the operator can release spring 50 with first latch 52 in order to puncture tissue. The "spring-loaded" construction of needle 24 imparts sufficient force to puncture tissue and maintains sufficient force on needle 24 to hold needle 24 in place once the desired location has been penetrated. Therefore, the release mechanisms disclosed herein advantageously free the operator from having to manually hold needle 24 in a retracted position during catheter positioning and from having to manually hold needle 24 in a deployed position during injection of a substance.

Figure 5:
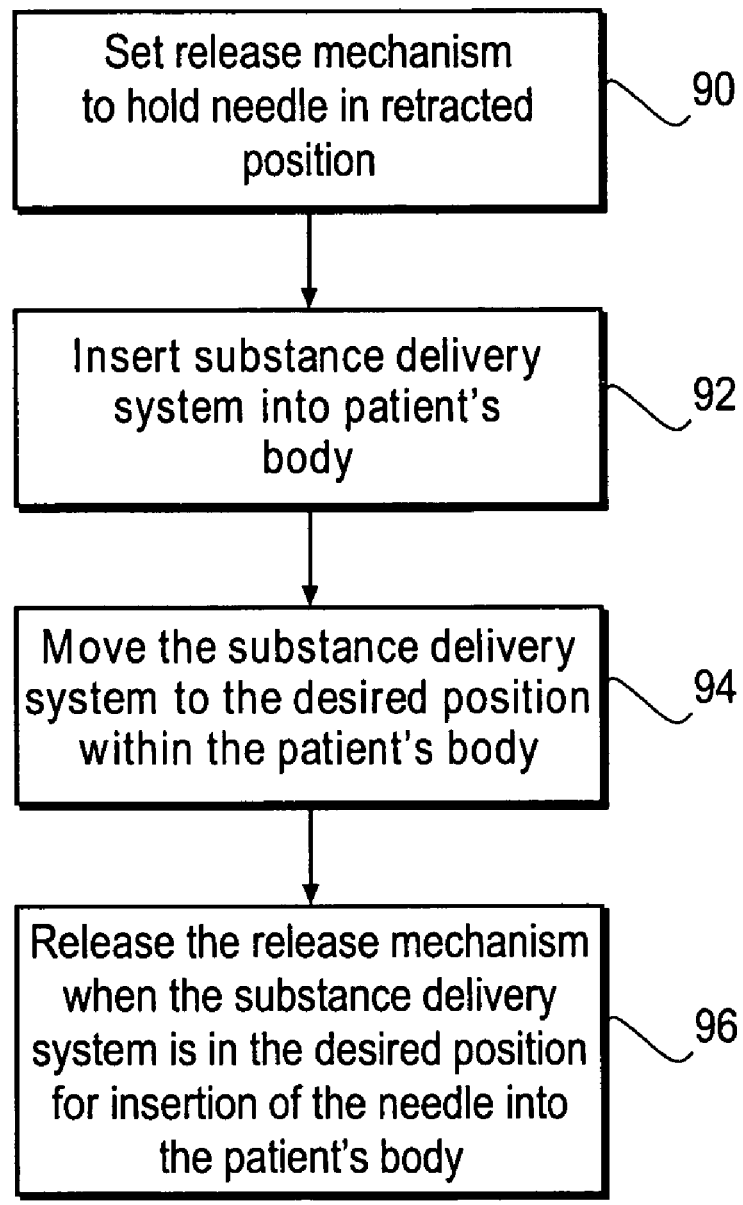
FIG. 5 is a flow chart showing a method of operating a substance delivery system that includes a guide catheter and a needle catheter.

Referring now to FIG. 5, a flow chart is shown detailing one method of using the embodiments disclosed herein. At block 90, the release mechanism is set to hold the needle in the retracted position. The substance delivery system (e.g., guide catheter and needle catheter) is inserted into the body of a patient at block 92.

If the guide catheter and needle catheter are separate devices, one of two methods could be used. First, the guide catheter could be inserted with a guide wire, the guide wire withdrawn, and the needle catheter inserted. Second, the guide catheter and needle catheter could be inserted together (either as a single device or one device disposed within the other, depending on construction).

Next, the substance delivery system is moved to a desired position within the body of the patient at block 94. When the operator is ready to penetrate tissue at block 96, the operator releases the release mechanism in order to puncture tissue at a desired location. At this point the operator will inject a substance into the punctured tissue, if necessary.

It is to be understood that even though numerous characteristics and advantages of various embodiments have been set forth in the foregoing description together with details of structure and function of the various embodiments, this disclosure is illustrative only. Changes may be made in detail, especially matters of structure and management of parts, without departing from the scope of the various embodiments as expressed by the broad general meaning of the terms of the appended claims.

I claim:

1. An apparatus comprising:
   a handle;
   a flexible body portion coupled to the handle, the flexible body portion having dimensions suitable for insertion into and navigation through a body, the flexible body portion defining a lumen therethrough and having a distal portion and a proximal portion, wherein the proximal portion comprises:
      a flexible element disposed around the lumen, and
      a braid disposed over the flexible element;
   a first plastic coating impregnated into the proximal portion of the flexible body portion;
   a second plastic coating impregnated into the distal portion of the flexible body portion;
   an anchor element disposed in the distal portion of the flexible body portion;
   a tendon wire having a distal end coupled to the anchor element and a proximal end coupled to the handle such that manipulation of the handle results in deflection of the distal portion of the flexible body portion; and
   an electrical interface electrically coupled to the tendon wire, wherein the anchor element and the tendon wire each comprise electrically conductive material such that an instrument can receive an electrical signal from the tendon wire through the electrical interface.

2. The apparatus of claim 1, wherein the anchor element comprises:
   at least one of a ring and an electrode.

3. The apparatus of claim 2, further comprising:
   a third plastic coating, stiffer than the second plastic coating, disposed on an area just proximal to the anchor element.

4. The apparatus of claim 1, wherein the flexible element is at least one of a coil and a second braid.

5. The apparatus of claim 4, wherein the flexible element is one of a single coil and a multi-filar coil.

6. The apparatus of claim 4, wherein the first braid is wound at an angle of approximately 55 degrees relative to a longitudinal axis of the flexible body portion.

7. The apparatus of claim 1, further comprising:
   a first piece of elastically deformable material disposed on a first area of the distal portion of the flexible body portion; and
   a second piece of elastically deformable material disposed on a second area of the distal portion of the flexible body portion, the second area located approximately 180 degrees from the first area.

8. The apparatus of claim 7, further comprising:
   a coil of elastically deformable material coupled to each of the first and second pieces of elastically deformable material.

9. The apparatus of claim 1, further comprising:
   a second lumen defined by the flexible body portion; and
   an elongate stabilizing member having a distal end, the stabilizing member to be disposed within the second lumen such that the distal end of the stabilizing member protrudes therefrom such that the distal end of the stabilizing member may be placed in a position within the body to act as a reference point for the flexible body portion.

10. The apparatus of claim 1, further comprising:
    a location sensor disposed on the distal portion of the flexible body portion, the location sensor to indicate a position of the distal portion of the flexible body portion within the body by at least one of an electromagnetic mapping system, a radio frequency mapping system, and an ultrasonic mapping system.

11. The apparatus of claim 1, further comprising:
    an accelerometer disposed on the distal portion of the flexible body portion, the accelerometer to obtain information regarding cardiac tissue motion.

12. A substance delivery system comprising:
    a guide catheter comprising
       a handle;
       a flexible body portion coupled to the handle, the flexible body portion having dimensions suitable for insertion into and navigation through a body, the flexible body portion defining a lumen therethrough and having a distal portion and a proximal portion, wherein the proximal portion comprises
          a flexible element disposed around the lumen, and
          a braid disposed over the flexible element;
       a first plastic coating impregnated into the proximal portion of the flexible body portion;
       a second plastic coating impregnated into the distal portion of the flexible body portion;
       an anchor element disposed in the distal portion of the flexible body portion; and
       a tendon wire having a distal end coupled to the anchor element and a proximal end coupled to the handle such that manipulation of the handle results in deflection of the distal portion of the flexible body portion; and
    a needle catheter to be disposed within the lumen of the guide catheter such that a distal end of the needle catheter can protrude from an opening in the distal end of the guide catheter, the needle catheter comprising
       a duplex spring impregnated with a third plastic coating,
       a braided shaft disposed over the duplex spring,
       a needle coupled to an inner diameter of the duplex spring,
       an electrode coupled to the distal end of the needle catheter, the electrode having an opening through which the needle is movable between a retracted position and a deployed position, an electrical insulator disposed between the needle and the electrode, and a needle control assembly comprising an elastically deformable element coupled to at least one of the duplex spring and the braided shaft of the needle catheter, and a release mechanism which releasably engages the elastically deformable element when the elastically deformable element is in a position which corresponds to the needle being in the retracted position.

13. The substance delivery system of claim 12 further comprising:

an electrical interface electrically coupled to the tendon wire, wherein the anchor element and the tendon wire each comprise electrically conductive material such that an instrument can receive an electrical signal from the tendon wire through the electrical interface.

14. The substance delivery system of claim 12, wherein the anchor element comprises at least one of a ring and an electrode.

15. The substance delivery system of claim 14, further comprising:

a fourth plastic coating, stiffer than the second plastic coating, disposed on an area just proximal to the anchor element.

16. The substance delivery system of claim 12, wherein the flexible element is at least one of a coil and a second braid.

17. The substance delivery system of claim 16, wherein the flexible element is one of a single coil and a multi-filar coil.

18. The substance delivery system of claim 16, wherein the first braid is wound at an angle of approximately 55 degrees relative to a longitudinal axis of the guide catheter.

19. The substance delivery system of claim 12, further comprising:

a first piece of elastically deformable material disposed on a first area of the distal portion of the flexible body portion; and a second piece of elastically deformable material disposed on a second area of the distal portion of the flexible body portion, the second area located approximately 180 degrees from the first area.

20. The substance delivery system of claim 19, further comprising:

a coil of elastically deformable material coupled to each of the first and second pieces of elastically deformable material.

21. The substance delivery system of claim 12, further comprising:

a second lumen defined by the flexible body portion; and an elongate stabilizing member having a distal end, the stabilizing member to be disposed within the second lumen such that the distal end of the stabilizing member protrudes therefrom such that the distal end of the stabilizing member may be placed in a position within the body to act as a reference point for the flexible body portion.

22. The substance delivery system of claim 12, further comprising:

a location sensor disposed on the distal portion of the flexible body portion, the location sensor to indicate a position of the distal portion of the flexible body portion within the body by at least one of an electromagnetic mapping system, a radio frequency mapping system, and an ultrasonic mapping system.

23. The substance delivery system of claim 12, further comprising:

an accelerometer disposed on at least one of the distal portion of the flexible body portion and a distal portion of the needle catheter, the accelerometer to obtain information regarding cardiac tissue motion.

24. The substance delivery system of claim 12, wherein the elastically deformable element comprises:

a spring.

25. The substance delivery system of claim 24, wherein the release mechanism comprises:

a housing having the spring disposed within the housing;

a stop disposed within the housing, distal to the spring, and coupled to at least one of the duplex spring and the braided shaft of the needle catheter;

a first latch pivotally coupled to the housing and having a movable portion biased towards the housing, the first latch having an angled portion and a flat portion, the flat portion to engage the stop when the needle is in the retracted position; and a second latch pivotally coupled to the housing and having a movable portion biased towards the housing, the second latch to releasably engage the first latch when the flat portion of the first latch is in contact with the stop in order to prevent the first latch from releasing the stop.

26. The substance delivery system of claim 12, further comprising:

a reference electrode coupled to at least one of the distal portion of the guide catheter, a distal portion of the needle catheter, and an outer surface of the body.

* * * * *